Feb. 26, 1957 E. S. BOERNER Plant Pat. 1,571
CHRYSANTHEMUM PLANT
Filed May 28, 1956
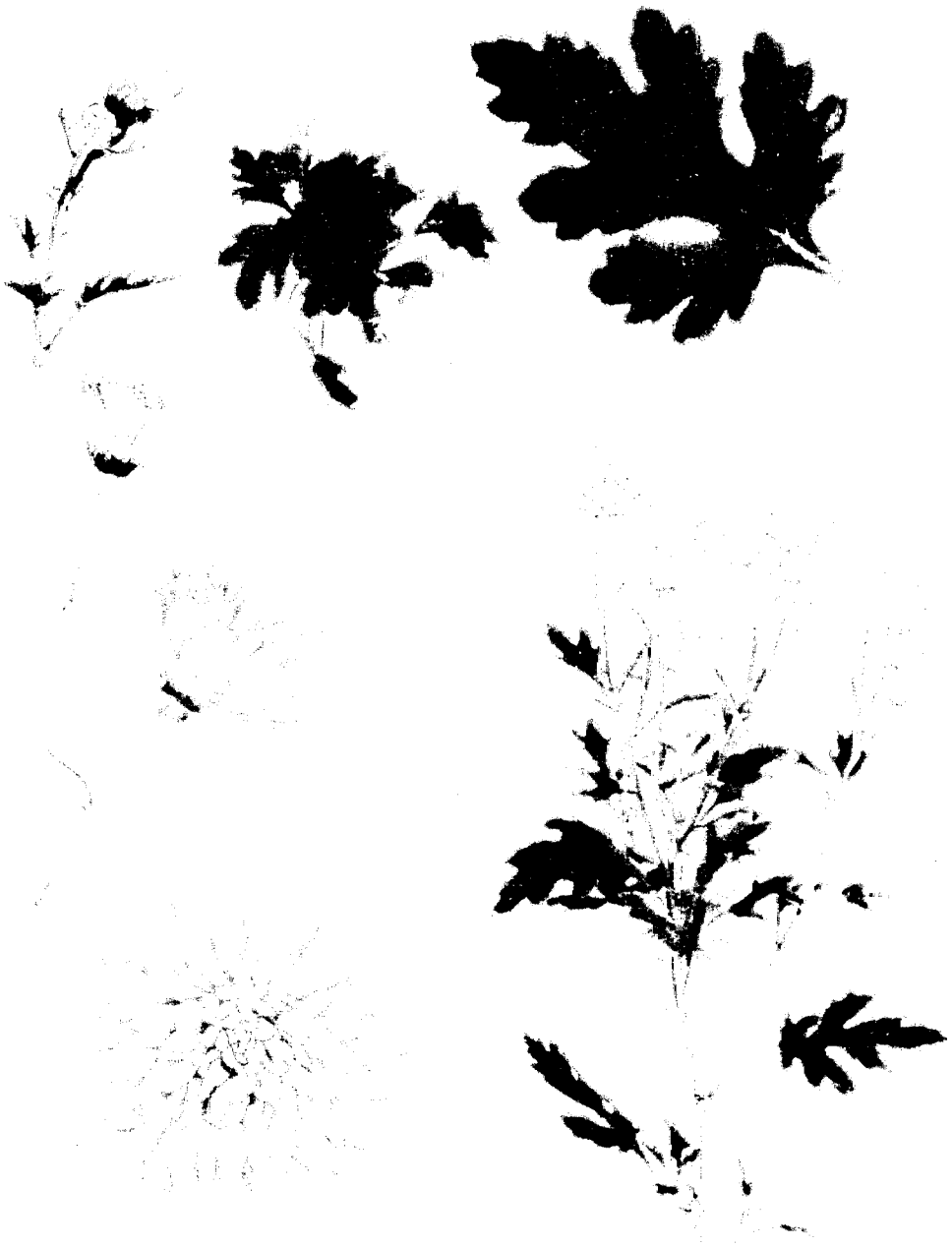
Inventor.
E. S. Boerner
By: Robb & Robb
Attorneys.

United States Patent Office

Plant Pat. 1,571
Patented Feb. 26, 1957

1,571

CHRYSANTHEMUM PLANT

Eugene S. Boerner, Newark, N. Y., assignor to Jackson & Perkins Company, Newark, N. Y., a corporation of New York Application May 28, 1956, Serial No. 587,915

1 Claim. (Cl. 47—60)

The present invention relates to a new and distinct variety of chrysanthemum plant of the decorative type, which was originated by me by crossing an unnamed and unpatented double pink-lavender seedling, derived from "September Dawn" (unpatented) × an unnamed and unpatented large-flowered seedling, with the variety "Kingbird" (Plant Patent No. 1306).

The primary objective of this breeding was to produce a new chrysanthemum variety which combines the upright growth, vigor and flower size of the "Kingbird" parent variety with a new flower color which is unique in the field of chrysanthemums. This objective was fully achieved, along with other improvements, as evidenced by the following features which are outstanding in my new variety:

(1) Upright and vigorous habits of growth;
(2) Clean foliage;
(3) Large size and profuse quantity of blooms; and
(4) A distinctive Pale Persian Lilac, lightly overcast with Rose Pink, general color tonality of the flowers.

The foregoing characteristics and distinctions definitely differentiate my new variety from its parents, as well as from all other varieties of its class of which I am aware, and asexual reproduction of the new variety by both top cuttings and underground runners, as performed by me at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: An unnamed double pink-lavender seedling derived from "September Dawn" × an unnamed large-flowered seedling × "Kingbird."
Classification: Decorative type.

Growth: Vigorous; strong; upright; about 30 inches tall.
Cold resistance: Plants are winter-hardy in northern New York, and flowers are very frost resistant.
Blooming period: In the Newark, N. Y., climatic area, blooming usually begins about September 30th and continues until heavy frosts.

*Flower*

(Observations made from specimens grown in a field at Newark, New York, in early October and about mid-morning.)

Bud:
*Color.*—When sepals first divide—Tourmaline Pink, Plate 38. When petals begin to unfurl—Amaranth Pink, Plate 12. When half-blown: inside of petals—Daphne Pink, Plate 38, lightly overcast with Tyrian Pink, Plate 12; reverse of petals—Pale Rose-Purple, Plate 26, lightly overcast with Light Rosolane Purple, Plate 26.
*Peduncle.*—Strong. Color—Kildare Green, Plate 31.
Bloom:
*Size.*—From 4 inches to 4½ inches.
*Stem.*—Long; strong.
*Form.*—Decorative.
*Petalage.*—Double.
*Color.*—Center of flower—Persian Lilac, Plate 38, lightly overcast with Amaranth Pink, Plate 12. Outer petals—Pale Persian Lilac, Plate 38, lightly overcast with Rose Pink, Plate 12. Base of petals—Glass Green, Plate 31. Inside of petals—Persian Lilac, Plate 38, lightly overcast with Light Rosolane Purple, Plate 26. Reverse of petals—Rosolane Pink, Plate 26.
*Petals.*—Texture—medium. Form—oval.
*Fragrance.*—Characteristic chrysanthemum.

*Plant*

Form: Upright.
Growth: Medium.
Foliage:
*Size.*—Average.
*Quantity.*—Abundant.
*Color.*—Upper side—Dark Dull Yellow-Green, Plate 32. Reverse side—Bice Green, Plate 17.
*Texture.*—Leathery; exceptionally clean.

I claim:

A new and distinct variety of chrysanthemum plant of the decorative type, substantially as herein shown and described, characterized particularly as to novelty by its upright and vigorous habits of growth, its clean foliage, the large size and profuse quantity of its blooms, and the distinctive Pale Persian Lilac, lightly overcast with Rose Pink, general color tonality of its flowers.

No references cited.